United States Patent
Takagi et al.

(10) Patent No.: US 6,451,580 B1
(45) Date of Patent: Sep. 17, 2002

(54) METHOD OF ENRICHING ORGANIC CONTAMINANT-DECOMPOSING BACTERIA IN POROUS MATERIAL FOR TREATING SOIL

(75) Inventors: Kazuhiro Takagi, Ibaraki; Yuuichi Yoshioka, Kochi, both of (JP)

(73) Assignee: National Institute for Agro-Environmental Sciences Independent Administrative Institute, Tsukuba (JP)

( * ) Notice: Subject to any disclaimer, the term of this patent is extended or adjusted under 35 U.S.C. 154(b) by 0 days.

(21) Appl. No.: 09/378,762

(22) Filed: Aug. 23, 1999

(51) Int. Cl.$^7$ .............................. B09B 3/00; C02F 3/30; C12N 1/00; C12N 1/12; C12N 1/20
(52) U.S. Cl. ...................... 435/243; 210/600; 210/605; 210/610; 424/93.1; 435/252.1; 435/262.5
(58) Field of Search .................................. 210/600, 610, 210/605; 435/262.5, 243, 252.1; 424/93.1

(56) References Cited

U.S. PATENT DOCUMENTS

| | | | |
|---|---|---|---|
| 5,653,675 A | * 8/1997 | Kanno et al. | 588/249 |
| 5,863,789 A | * 1/1999 | Komatsu et al. | 435/262 |
| 6,087,547 A | * 7/2000 | Marton et al. | 588/206 |

* cited by examiner

Primary Examiner—David M. Naff
Assistant Examiner—Deborah K. Ware
(74) Attorney, Agent, or Firm—Rader, Fishman & Grauer PLLC

(57) ABSTRACT

A porous material having a greater adsorptivity for adsorbing organic contaminants, such as agricultural chemicals, than a target soil, is fragmented. The fragmented porous material is mixed into a soil which the decomposing bacteria inhabit, thereby forming an enrichment soil layer. Through the enrichment soil layer, there is circulated an inorganic salt medium containing carbon and nitrogen sources formed by only an organic contaminant to be decomposed, thereby rapidly enriching the decomposing bacteria in the fragmented porous material. The fragmented porous material is inoculated into new fragmented porous material to form an enrichment layer consisting of the fragmented porous material only. Into the enrichment layer, the inorganic salt medium containing carbon and nitrogen sources formed by only an organic contaminant to be decomposed is circulated and the operation of enriching decomposing bacteria is repeated a plurality of times for the new fragmented porous material as well to enhance the degree of purity and enrichment of the decomposing bacteria, thereby rapidly isolating the decomposing bacteria.

9 Claims, 7 Drawing Sheets

Fig.3

| ARTIFICIAL MICROHABITAT | pH (H₂O) | BET-SINGLE POINT DETERMINATION SPECIFIC AREA (m²/g) | PERCENTAGE OF CUMULATIVE MICROPORE VOLUMES CALCULATED FOR RESPECTIVE RANGES OF DIAMETERS OF MICROPORES (%) DIAMETER OF MICROPORES (μm) | | | | | | | |
|---|---|---|---|---|---|---|---|---|---|---|
| | | | 200~100 | 100~50 | 50~20 | 20~10 | 10~5 | 5~1 | 1~0.003 |
| A | 7.8 | 99.9 | 3.0 | 6.5 | 9.8 | 6.4 | 5.8 | 16.5 | 52.3 |
| B | 5.5 | 72.1 | 5.4 | 4.3 | 9.0 | 6.6 | 5.4 | 9.3 | 60.1 |
| C | 10.4 | 208.6 | 0.0 | 2.5 | 17.5 | 12.0 | 1.5 | 14.8 | 51.7 |
| D | 8.1 | 555.7 | 0.0 | 2.5 | 20.0 | 25.4 | 7.5 | 22.5 | 22.1 |
| E | 9.6 | 1020.9 | 0.8 | 0.9 | 1.4 | 1.8 | 3.2 | 29.0 | 63.2 |

| | Kf | 1/n |
|---|---|---|
| SOIL | 2.4 | 0.93 |
| A | 39.8 | 0.69 |
| B | 36.1 | 1.02 |
| C | 677.6 | 1.18 |
| D | 11508.0 | 1.29 |
| E | 22438.8 | 1.06 |

Kf: ADSORPTION COEFFICIENT,
n: FREUNDLICH EXPONENT

| ARTIFICIAL MICROHABITAT | MICROBIAL BIOMASS (mg C/kg d.s.) | NUMBER OF BACTERIA ( /g d.m.) CFU×10$^8$ |
|---|---|---|
| A | 7884.2 | 1.7 |
| B | 10214.0 | 3.5 |
| C | 3828.6 | - |
| D | 5651.1 | 1.9 |
| E | 2112.5 | - |

METHOD OF ENRICHING ORGANIC CONTAMINANT-DECOMPOSING BACTERIA IN POROUS MATERIAL FOR TREATING SOIL

BACKGROUND OF THE INVENTION

1. Field of the Invention

This invention relates to a technique of enrichment of decomposing bacteria which can be used to treat soil polluted by organic contaminants, such as agricultural chemicals, particularly to prevent groundwater pollution caused by agricultural chemicals in soil and a technique of isolating the decomposing bacteria by utilizing the enriching technique, and more particularly to techniques of these kinds which make it possible to drastically reduce time required for the enrichment or isolation of the decomposing bacteria.

2. Prior Art

To maintain today's agricultural production, agricultural chemicals cannot be dispensed with, and to conserve flora in golf courses or the like as well, agricultural chemicals are used in large quantities. On the other hand, there is a concern that agricultural chemicals work as contaminants to have undesirable effects on the environment, especially to be a pollution source of groundwater. To eliminate this threat, it is desired to develop a technique of effectively preventing agricultural chemicals from remaining or spreading in the environment as contaminants after they have served their functions.

A great variety of microorganisms on the order of billions/1 g live in soils, and among these microorganisms there are not a few decomposing bacteria which are capable of decomposing organic compounds serving as functional skeletons in a lot of agricultural chemicals, thereby defusing the organic compounds or eliminating the same from the environment. Therefore, it is possible to thereby eliminate contaminants, such as agricultural chemicals or the like, from the environment by exploiting such capabilities of the decomposing bacteria. Generally, however, under natural conditions, decomposing bacteria capable of decomposing or degrading specific kinds of organic compounds are too thinly populated to effectively prevent contaminants from remaining or spreading in the environment. Therefore, a method of selectively enriching such decomposing bacteria and isolating the same from soil and thereafter applying the same to soil again is considered to be powerful means for preventing groundwater pollution by soil contaminated by organic compounds, such as agricultural chemicals and the like.

The method of selective enrichment/isolation of specific kinds of bacteria from diverse soil-inhabiting bacteria includes a soil percolation technique in which a column or the like is filled with soil containing inhabiting decomposing bacteria to form an enrichment soil layer, and inorganic salt medium, which contains only contaminants, such as agricultural chemicals, as solo carbon and nitrogen sources, is continuously circulated through the enrichment soil layer, whereby a specific kind of decomposing bacteria, that is, decomposing bacteria which are capable of using the carbon or nitrogen source contained in the inorganic salt medium for assimilation are selectively enriched for isolation. In the case of the above conventional soil percolation technique, generally a time period of one half to one year is required to enrich and isolate decomposing bacteria for practical use, which is a large impediment encountered in putting to practical use a groundwater pollution control technique and a soil cleanup technique using decomposing bacteria.

SUMMARY OF THE INVENTION

The present invention has been made under these circumstances, and its object is to provide a method of enriching decomposing bacteria which is capable of realizing bacteria-enriching/isolating speeds required high enough to put to practical use the groundwater pollution control technique using decomposing bacteria, and a method of isolating the decomposing bacteria by using the enriching method.

This invention is based on the following new finding: It is possible to improve the above soil percolation technique by adding an artificial microhabitat having a specific characteristic to an enrichment soil layer and thereby largely enhance the speed of enrichment of decomposing bacteria and the speed of isolation of the same from the soil.

According to the study of the present inventors, it has been found that if a porous material having an infinite number of micropores, such as charcoal, is fragmented to pieces of approximately several mm to ten and several mm in size such that the same can be handled with ease and at the same time has a large effective surface area, and then the fragmented porous material is mixed into an enrichment soil layer as an artificial microhabitat, decomposing bacteria can be effectively enriched and isolated over a time period of three weeks to three months, although they are slightly different depending on the kind of a contaminant and the kind of bacteria decomposing the contaminant. Such high-speed enrichment and isolation are not only far more excellent than the conventional methods requiring a time period of one half to one year, but also can sufficiently meet requirements for putting to use the technique of controlling pollution of groundwater by using the, decomposing bacteria.

Such high-speed enrichment and isolation is considered to be enabled by the following mechanism: First, the artificial microhabitat formed of the porous material efficiently adsorbs contaminants, that is, carbon and nitrogen sources, contained in an inorganic salt medium, into its infinite number of micropores mainly by hydrophobic adsorption to decompose bacteria. Further, under preferred conditions provided by the micropores of the artificial microhabitat, the decomposing bacteria can actively proliferate and be active in the micropores. These factors cooperate so that the decomposing bacteria in the micropores efficiently decompose or degrade the contaminants efficiently adsorbed in the micropores. As a result, the high-speed enrichment can be realized. In other words, by using the artificial microhabitat, the contaminants per se can be collected with efficiency in the artificial microhabitat, and moreover the artificial microhabitat can promote the growth of the decomposing bacteria, thereby enabling the high-speed enrichment of the bacteria. This also works effectively when artificial microhabitats containing enriched decomposing bacteria are used in farms and golf courses as a material for prevention of groundwater pollution, realizing a more efficient groundwater control capability.

In isolating decomposing bacteria through enhanced enrichment of the same, it goes without saying that the above-described mechanism works, but further, high-speed isolation of the decomposing bacteria is realized by isolating operations effectively carried out through the fact that enriched decomposing bacteria can be easily taken out from soil in the form of a treatable artificial microhabitat, and that by using the microhabitat, it is possible to easily inoculate the taken-out bacteria in new artificial microhabitats, and further that by circulation, it is possible to purify and enrich the bacteria in the artificial microhabitat.

One of the conditions for effectively activating the above-described mechanism is that a porous material as artificial microhabitats has a greater adsorptivity for adsorbing organic contaminants than a target soil.

According to the study of the present inventors, a more preferable condition of the porous material is that it has an adsorption coefficient ($K_f$) larger than scores of times and at the same time smaller than thousands of times as large as that of a soil used for an enrichment soil layer. Such a condition is substantially equivalent to a condition that the porous material has a specific surface area larger than approximately 50 $m^2$/g and at the same time smaller than about 600 $m^2$/g.

The reason for making these conditions preferable is related to the above-described mechanism. That is, if a porous material has an adsorptivity larger than required, it is impossible to cause adsorption of organic contaminants such that the decomposing bacteria are capable of effectively using the contaminants, more specifically, it is impossible to cause the organic contaminants to be efficiently adsorbed in micropores having suitable sizes for the bacteria to readily inhabit, in a state permitting the decomposing bacteria to make use of the organic contaminants. In other words, in such a case, an excessively large amount of organic contaminants are adsorbed in micropores other than ones where the bacteria can inhabit. Further, the excessively large adsorptivity of a porous material leads to degraded contaminant-decomposing efficiency thereof when the porous material containing the enriched decomposing bacteria is used as a material for prevention of groundwater pollution. That is, the requirement of an appropriate adsorptivity of a porous material contributes to an enhanced functionality of the porous material containing the enriched decomposing bacteria when it is used as a material for prevention of groundwater pollution, as well.

In addition to the above conditions, a predetermined condition set to distribution of the micropores in a porous material can make the above mechanism function more effectively. According to the study of the present inventors, this condition is that a volume ratio of micropores having sizes permitting the decomposing bacteria to form colonies to a total of micropores is equal to or larger than 10%. More specifically, when charcoal is taken as an example of the porous material, micropores thereof generally have a large range of diameter distribution from an order of nanometer to an order of hundreds of micrometer. of these micropores, those where decomposing bacteria are ready to settle and further capable of forming stable colonies have a diameter of 2 to 50 $\mu$m, in general, and particularly, micropores having a diameter of 5 to 20 $\mu$m are most suitable for decomposing bacteria. Therefore, a porous material having micropores of the above-mentioned sizes at a volume ratio equal to or higher than a predetermined value is suitable for an artificial microhabitat, and as the ratio becomes higher, the porous material becomes more suitable for an artificial microhabitat. Although this condition is somewhat related to the above-mentioned adsorptivity or specific surface area, it is not equivalent to any of these properties.

Therefore, the method of enriching decomposing bacteria according to the present invention aims to enrich a specific kind of bacteria capable of decomposing organic contaminants contained in soil. Hence, the enrichment method is characterized by comprising the steps of: mixing a fragmented porous material having an infinite number of micropores and a greater adsorptivity for adsorbing the organic contaminants than a target soil into a soil which the decomposing bacteria inhabit to form an enrichment soil layer, and circulating through the enrichment soil layer an inorganic salt medium containing carbon and nitrogen sources, the carbon and nitrogen sources being formed by only an organic contaminant to be decomposed, thereby enriching the decomposing bacteria in the fragmented porous material.

Further, in the enriching method according to the present invention, it is required as a preferred condition that the porous material has an adsorption coefficient ($K_f$) larger than scores of times and at the same time smaller than thousands of times as large as an adsorption coefficient ($K_f$) of the soil used for the enrichment soil layer, or that the porous material has a specific surface area larger than approximately 50 $m^2$/g and at the same time smaller than 600 $m^2$/g.

Further, in the enriching method according to the present invention, it is required as a more preferred condition that a volume ratio of micropores of the porous material having sizes permitting the decomposing bacteria to settle to a total of micropores of the porous material is equal to or larger than 10%.

The method of isolating decomposing bacteria according to the invention aims to isolate decomposing bacteria by using the enrichment method described above, and is characterized by comprising the steps of: inoculating a fragmented porous material in which the decomposing bacteria have already been enriched into a new fragmented porous material to form an enrichment layer consisting of the fragmented porous materials only, repeatedly carrying out a plurality of times an operation of enriching the decomposing bacteria in the new fragmented porous material as well by circulating through the enrichment layer an inorganic salt medium containing a carbon source and a nitrogen source, the carbon source and the nitrogen source being formed by only an organic contaminant to be. decomposed, thereby increasing a degree of purity and enrichment of the decomposing bacteria, for speedy isolation of the enriched decomposing bacteria.

As the porous material used in the present invention, there may be mentioned charcoal baked under a specific condition as a typical example. Especially, charcoal of broad-leaved tree, which is baked at a low or medium temperature of approximately 400 to 700° C. is suitable and such charcoal satisfies the conditions concerning the adsorptivity and specific surface area as well as the micropore distribution, described above. Further, it is also possible to use a synthetic appetite material which has been made porous, and an inorganic foam, such as a ceramic foam. These porous materials are excellent in that none of them adversely affect soil.

The present invention is by no means limited to the above description, but the objects, advantages, features, and use of the invention will become more apparent from the following detailed description taken in conjunction with the accompanying drawings. Further, it should be understood that all modifications properly made to the invention without departing from the spirit of the invention fall within the scope of the invention.

BRIEF DESCRIPTION OF THE DRAWINGS

FIG. 3 shows a table showing physical properties of each artificial microhabitat used in Experimental example 1;

DETAILED DESCRIPTION OF THE PREFERRED EMBODIMENT

Figure 1:
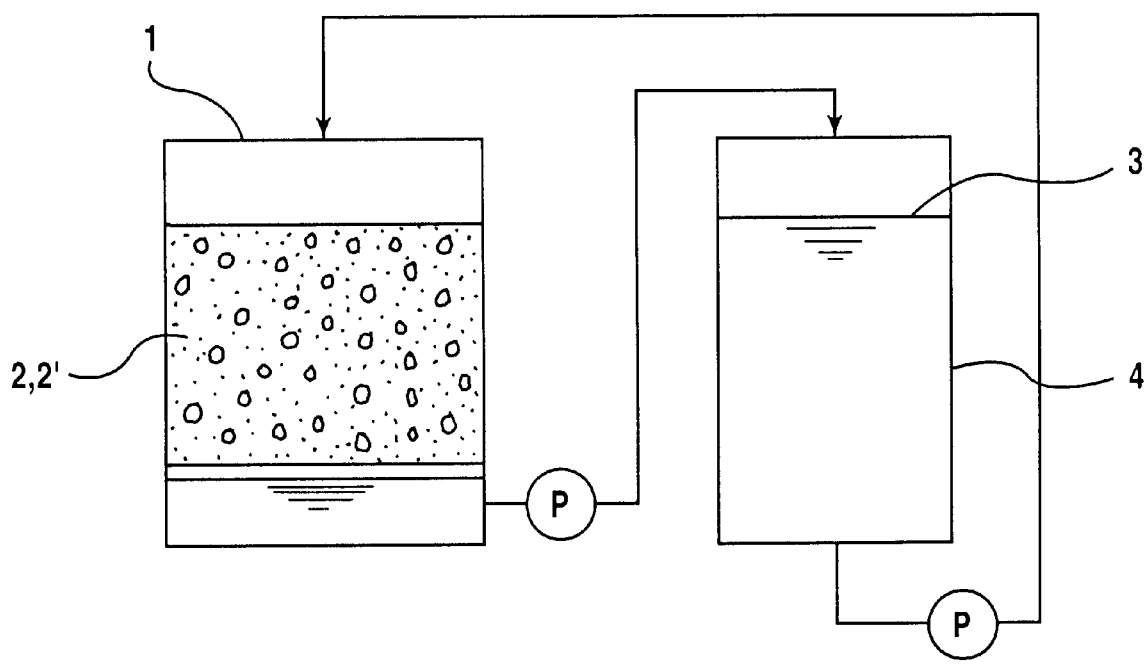
FIG. 1 is a diagram schematically showing a device used in a method of enriching decomposing bacteria according to an embodiment of the invention.
Figure 2:
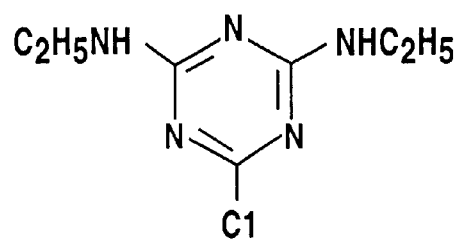
FIG. 2 is a diagram showing a chemical structure of simazine.

The present invention will now be described in detail with reference to the drawings showing an embodiment thereof. As shown in FIG. 1, according to an embodiment of the present invention, a soil layer 2 for enrichment of bacteria is formed in a soil layer storage tank 1. The enrichment soil layer 2 is formed by mixing 5% by weight charcoal, which is fragmented into pieces of 5 to 10 mm in size for use as an artificial microhabitat, into a soil which contaminant-decomposing bacteria inhabit. An inorganic salt medium 3 containing only a kind of organic contaminant to be decomposed, such as simazine (its chemical structure is shown in FIG. 2), as carbon: and nitrogen sources, is caused to circulate from a solution storage tank 4 to the enrichment soil layer 2. This circulation is continued for approximately three weeks, thereby enabling enrichment of the contaminant-decomposing bacteria to proceed to a sufficient extent.

The concentration of residual simazine in the circulating solution, and the concentration of by-products of decomposition or degradation of the simazine, e.g. $Cl^-$, are measured to thereby monitor the state of enrichment of the contaminant-decomposing bacteria. If a predetermined enrichment level is attained, then, an operation for isolating the decomposing bacteria is carried out. To carry out the isolating operation, first, the artificial microhabitat is taken out from the enrichment soil layer 2 as shown in FIG. 1. Then, the artificial microhabitat in which the decomposing bacteria has been already enriched is inoculated into another artificial microhabitat, whereby an enrichment layer 2' comprised of only the artificial microhabitats is formed (See FIG. 1) to carry out the same circulating operation as described above for this enrichment layer 2' in an apparatus having the same structure as that of FIG. 1. Such an operation is repeated appropriate times, e.g. approximately three times, whereby the degree of purity and enrichment of the decomposing bacteria is enhanced for speedy isolation.

EXPERIMENTAL EXAMPLES

Experimental example 1: an example of experiment will be described in which simazine is employed as an organic contaminant and artificial microhabitats are mixed into soil and simazine-decomposing bacteria are rapidly enriched in the artificial microhabitats, and the obtained, artificial microhabitats with enriched simazine-decomposing bacteria are inoculated into a plurality of artificial microhabitats different from each other in adsorptivity and micropore distribution and circulation experiments are performed to compare the enrichment rates of them with each other. The experimental conditions are as follows.

agricultural chemical to be tested: standard product of simazine;

soil to be tested: soil of a field repeatedly using simazine, sieved to soil material having a size of 2 mm or less;

circulating solution: inorganic salt medium containing only 5 mg/liter of simazine as solo carbon and nitrogen sources;

circulating conditions: 25° C., a dark place;

As artificial microhabitats, the following materials A to E were used. The physical properties of the artificial microhabitats are listed in Table of FIG. 3;

A: charcoal formed by normally baking a wood of broad-leaved tree and fragmenting to pieces of 5 to 10 mm;

B: chitosan-treated charcoal formed by normally baking a wood of broad-leaved tree and fragmenting to pieces of 5 to 10 mm;

C: charcoal formed by further baking the charcoal formed by normally baking the wood of broad-leaved tree, at 1000° C. for 4 hours, and fragmenting to pieces of 5 to 10 mm;

D: charcoal formed by baking conifer wood at 1000° C. for 8 hours and fragmenting to pieces of 5 to 10 mm;

E: commercially available granular activated carbon (grain diameter of 5 mm);

Chitosan treatment herein means that the charcoal is soaked in an acetic acid solution of chitosan, thereafter drying the same, thereby applying a coating of chitosan to inner walls of micropores of the charcoal. This treatment makes it possible to enhance the suitability of the charcoal as a habitat of decomposing bacteria by making pH ($H_2O$) of the charcoal, which generally tend to be alkaline, weakly acid to slightly alkaline, that is, from about 5.5 to 8.

Figures 4, 5:
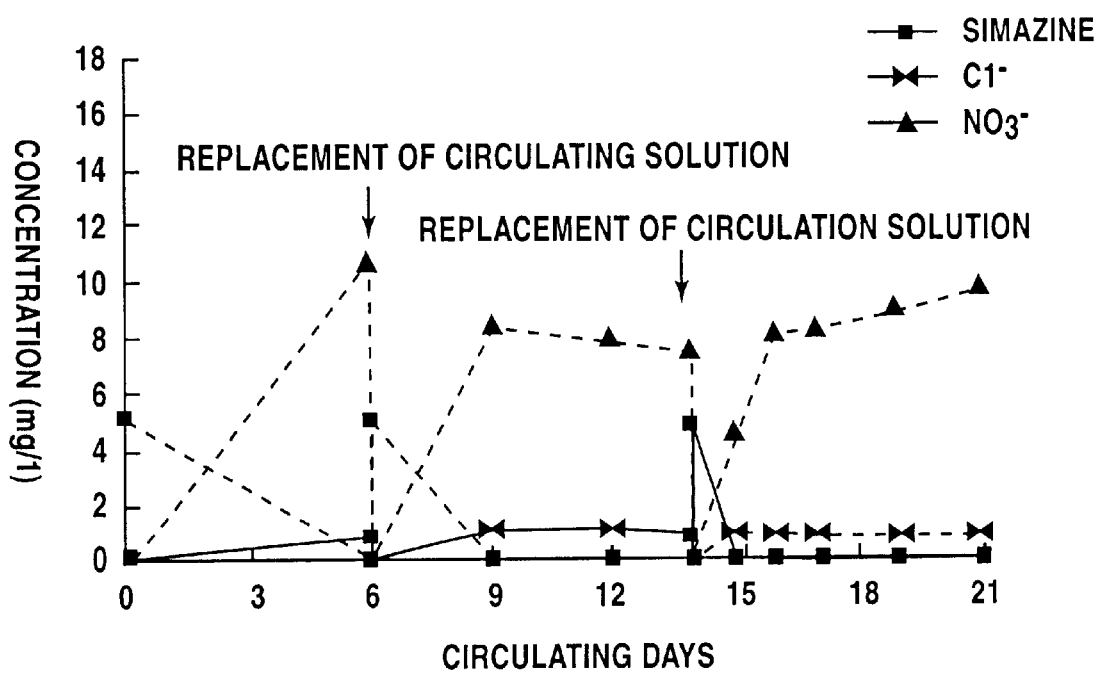
FIG. 4 shows a table showing differences in adsorptivity of simazine between soil and artificial microhabitats used in Experiment 1.
FIG. 5 shows a graph showing changes of concentrations of simazine, $Cl^-$ and $NO_3^-$ in a simazine-containing circulating solution in the process of Experimental example 1 in which decomposing bacteria are enriched in artificial microhabitats from an enrichment soil layer.
Figure 6:
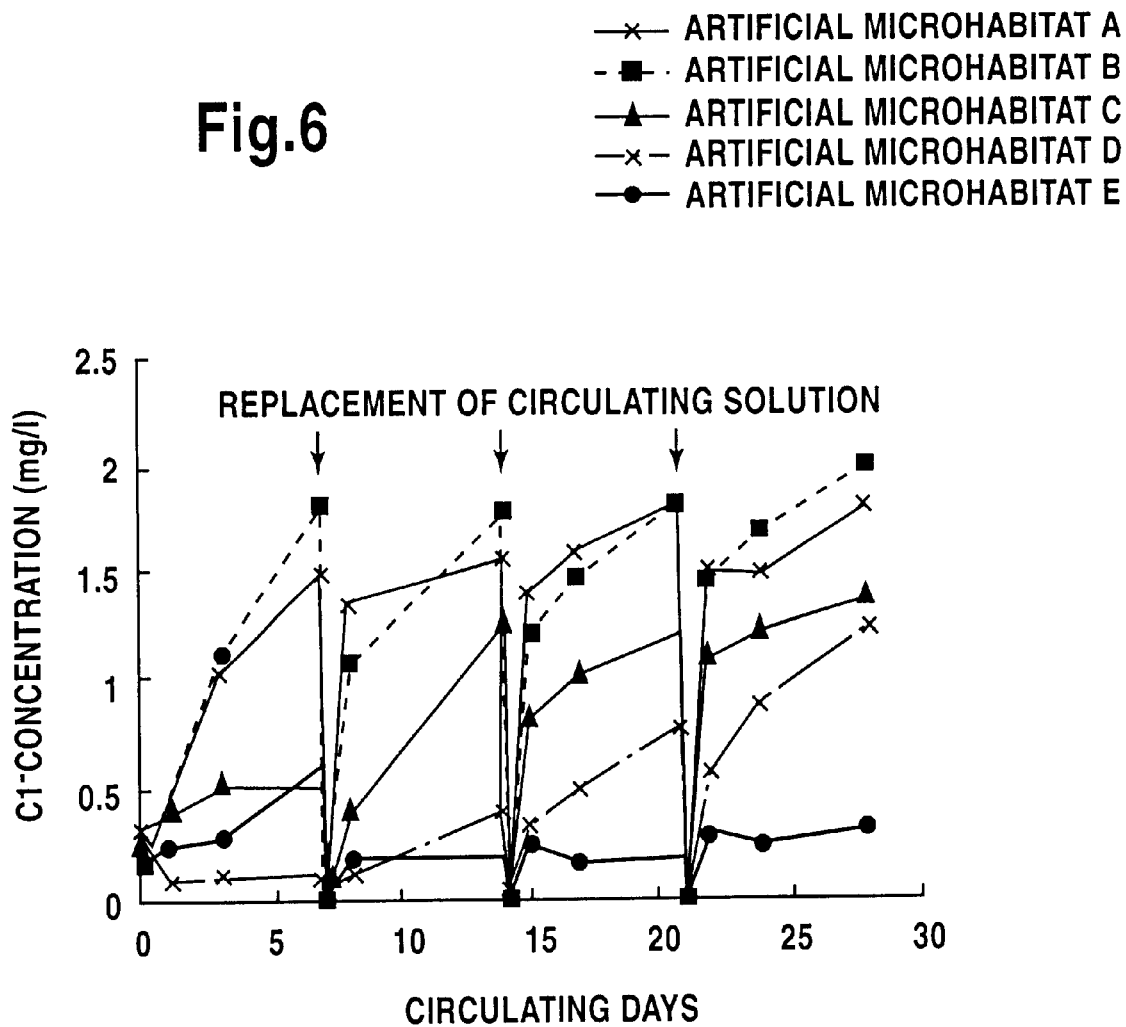
FIG. 6 shows a graph showing differences in enriching speeds of simazine-decomposing bacteria in the respective artificial microhabitats in relation to concentrations of $Cl^-$ in the process of Experimental example 1 in which respective artificial microhabitats are inoculated into an enrichment layer and a circulation treatment is performed to enhance the degree of purity and enrichment of decomposing bacteria.
Figures 7, 8:
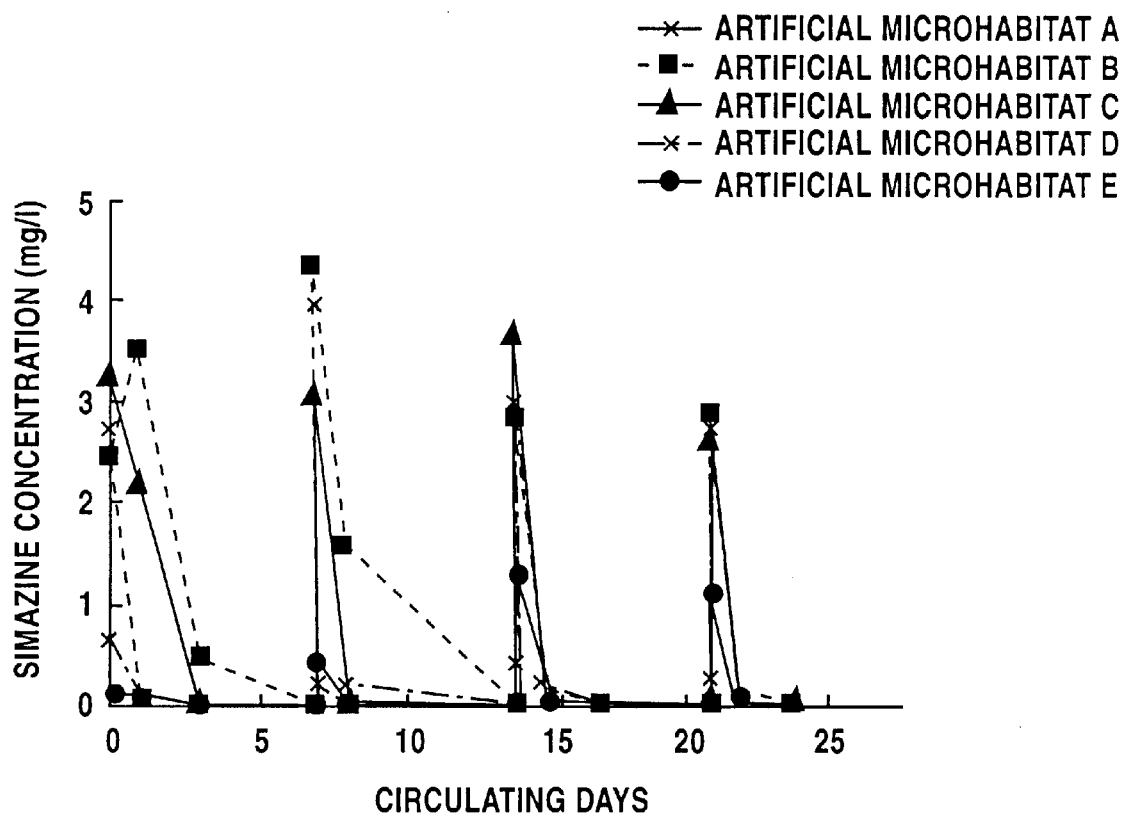
FIG. 7 shows a graph showing differences in the enriching speeds of the simazine-decomposing bacteria in the respective artificial microhabitats in relation to concentrations of simazine in the process of Experimental example 1 in which respective artificial microhabitats are inoculated into an enrichment layer and a circulation treatment is performed to enhance the degree of purity and enrichment of decomposing bacteria.
FIG. 8 shows a table which shows microbial biomasses and the numbers of living bacteria in the respective artificial microhabitats in Experimental example 1, measured four weeks after a medium circulation started.

The results of the experiments carried out under the above conditions are shown in a table in FIGS. 4 and graphs in FIGS. 5 to 7 and a table in FIG. 8. The table in FIG. 4 shows differences in adsorptivity of the simazine between soil and the artificial microhabitats A to E. The graph in FIG. 5 shows changes in the concentrations of the simazine, $Cl^-$, and $NO_3^-$ in the simazine-containing circulating solution, respectively, in the process of Experimental example 1 in which decomposing bacteria are enriched in artificial microhabitats from an enrichment soil layer. The graph in FIG. 6 shows differences in the enriching rates of the simazine-decomposing bacteria in the respective artificial microhabitats in relation to the concentrations of $Cl^-$ in the process of Experimental example 1 in which respective artificial microhabitats are inoculated into an enrichment layer and a circulation treatment is performed to enhance the degree of purity and enrichment of decomposing bacteria. The graph in FIG. 7 shows similar differences in relation to the concentrations of the simazine. And the table in FIG. 8 shows microbial biomasses and the numbers of living bacteria in the respective artificial microhabitats measured four weeks after the circulation started. These graphs and tables show that the enriching capabilities of the artificial microhabitats are different from each other according to the physical properties of porous materials used for making the artificial microhabitats (See FIG. 6 and FIG. 7), that the artificial microhabitats A to D have adsorptivity scores of times to thousands of times higher than that of the soil (See the values of $K_f$ as shown in FIG. 4), that the charcoal of conifer wood is considerably inferior in enriching capability to the charcoal of broad-leaved tree which has an appropriate specific surface area and micropore distribution (See FIG. 6 and FIG. 7), and that a practical enriching capacity can not be obtained from the activated carbon which is inappropriate in specific surface area and micropore distribution (See FIG. 6 and FIG. 7). This can be ensured by the measurement values of the microbial biomasses as shown in the table of FIG. 8.

It is recognized that if an artificial microhabitat made of charcoal of broad-leaved tree is used, increases in the $Cl^-$ concentrations are recognized in a week or so after the circulation started. This indicates that the enrichment of the decomposing bacteria is in progress and accordingly progressively activating the degradation of the simazine, and that about three weeks of circulation enables the sufficient enrichment of the bacteria as shown in FIG. 5. It should be noted that the numbers of living bacteria in the artificial microhabitats C and E just happen to be not counted, and hence they are not shown. The explanation "Replacement of circulating solution" provided in the graphs of FIGS. 4 and 5 means that a circulating solution in use was replaced by a newly prepared solution at each indicated time point.

Experimental example 2; another example of experiment will be described in which an experiment is carried out by a soil percolation technique assuming that in order to control groundwater pollution, artificial microhabitats containing enriched simazine-degrading bacteria are applied to soil at a golf course continuously using simazine, and the groundwater pollution-controlling functions of the artificial microhabitats are compared with those obtained in another experiment using artificial microhabitats without enrichments of simazine-degrading bacteria. The conditions of the experiments are indicated below.

Experimental conditions of artificial microhabitats with enrichments of simazine-degrading bacteria agricultural chemical to be tested: standard product of simazine;

soil to be tested: soil of a golf course continuously using simazine, sieved to soil material having a size of 2 mm or less;

artificial microhabitat a to be tested: chitosan-treated charcoal formed by normally baking a wood of broad-leaved tree and fragmenting to pieces of 5 to 10 mm, in which enrichment of the simazine-decomposing bacteria was carried out under the same conditions as those of the above Experimental example 1;

an artificial microhabitat b to be tested: charcoal formed by normally baking a wood of broad-leaved tree and fragmenting to pieces of 5 to 10 mm, in which the simazine-decomposing bacteria were enriched under the same conditions as those of the above Experimental example 1;

mixing ratio of artificial microhabitats a and b to the soil to be tested: 1.25% by weight;

circulating solution: inorganic salt medium containing only 5 mg/liter of simazine as carbon and nitrogen sources;

circulating conditions: 25° C., a dark place.

Experimental conditions of artificial microhabitats without enrichments of simazine-decomposing bacteria agricultural chemical to be tested: standard product of simazine;

soil to be tested: soil of a golf course continuously using simazine, sieved to soil material having a size of 2 mm or less;

artificial microhabitat c to be tested: chitosan treated charcoal formed by normally baking a wood of broadleaved tree and fragmenting to pieces of 5 to 10 mm, without enrichment;

an artificial microhabitat d to be tested: charcoal formed by normally baking a wood of broad-leaved tree and fragmenting to pieces of 5 to 10 mm, without enrichment;

mixing ratio of artificial microhabitats c and d to the soil to be tested: 2.5% by weight;

circulating solution: inorganic salt medium: containing only 5 mg/liter of simazine as carbon and nitrogen sources;

circulating conditions: 25° C., a dark place.

The above experimental conditions substantially realize conditions under which agricultural chemicals are regularly sprayed in golf courses at time intervals of several days. The results of the present experiment are shown in graphs of FIGS. 9 to 12. The graphs show changes in the concentrations of simazine, $Cl^-$ and $NO_3^-$ in the circulating solutions in the experiments concerning the respective artificial microhabitats a to d.

Figure 9:
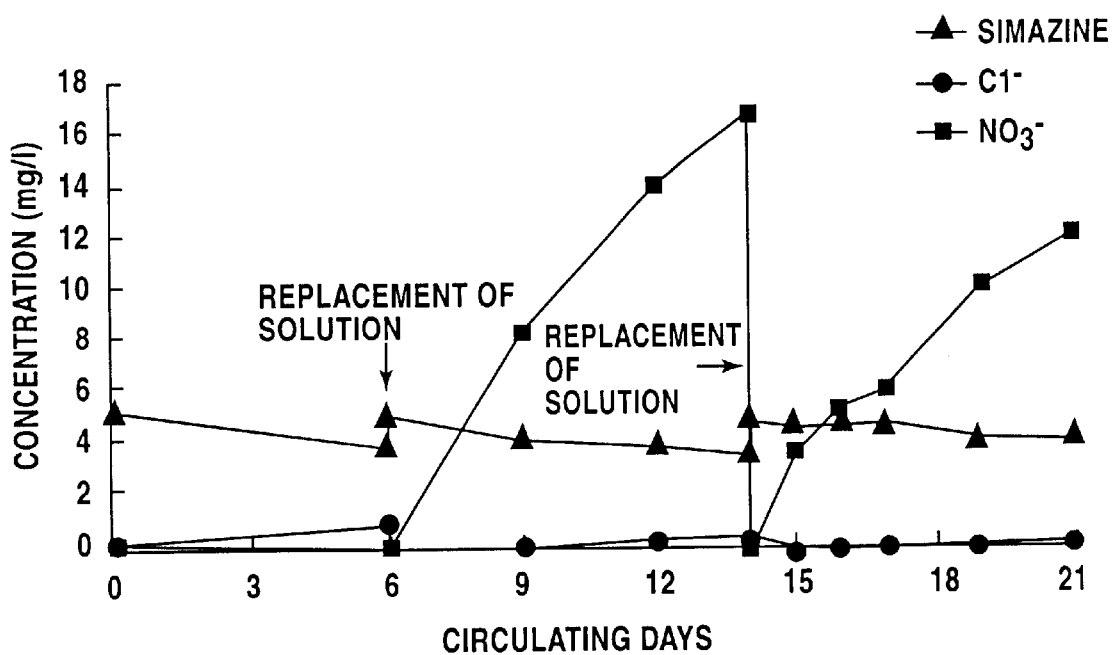
FIG. 9 shows a graph showing changes in concentrations of the simazine, $Cl^-$ and $NO_3^-$ in the simazine-containing circulating solution for an artificial microhabitat c without enrichments of simazine-decomposing bacteria, in Experimental example 2.
Figure 10:
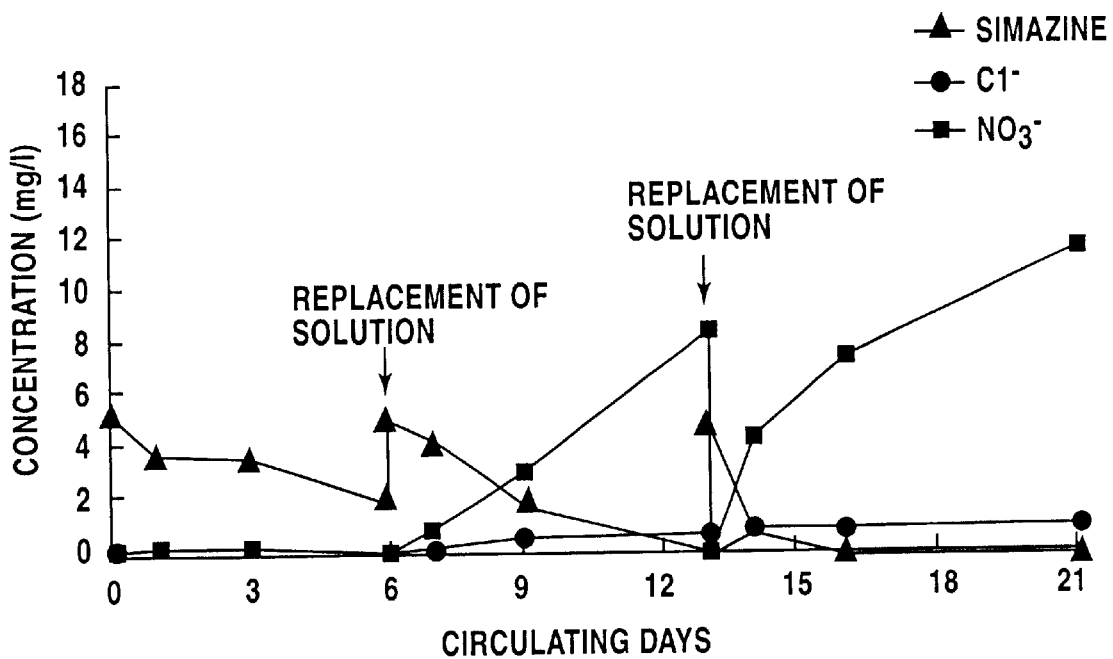
FIG. 10 shows a graph showing changes in concentrations of the simazine, $Cl^-$ and $NO_3^-$ in the simazine-containing circulating solution for an artificial microhabitat a with enrichments of simazine-decomposing bacteria, in Experimental example 2.
Figure 11:
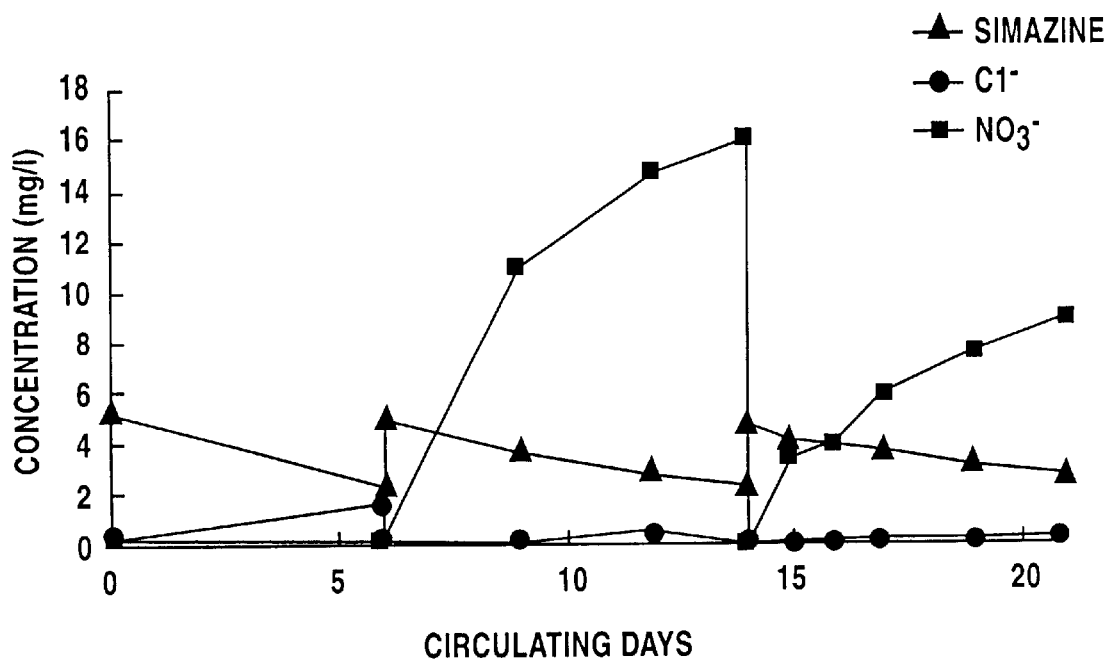
FIG. 11 shows a graph showing changes in concentrations of the simazine, $Cl^-$ and $NO_3^-$ in the simazine-containing circulating solution for an artificial microhabitat d without enrichments of simazine-decomposing bacteria, in Experimental example 2.
Figure 12:
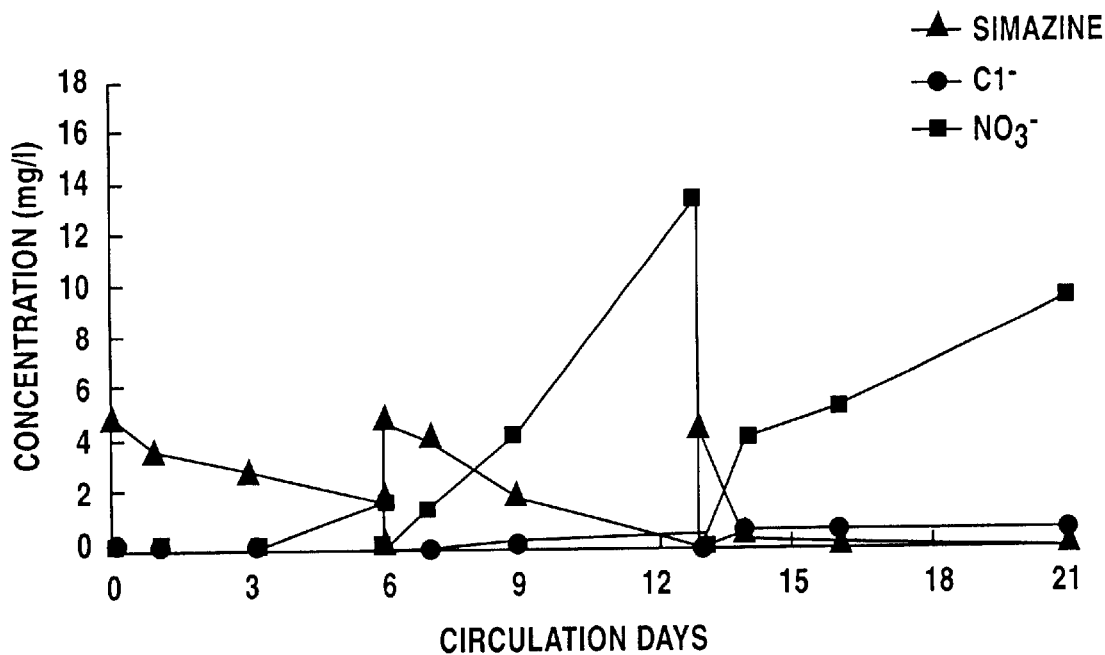
FIG. 12 shows a graph showing changes in concentrations of the simazine, $Cl^-$ and $NO_3^-$ in the simazine-containing circulating solution for an artificial microhabitat b with enrichments of simazine-decomposing bacteria, in Experimental example 2.

When attention is paid to the simazine concentration in each graph, the graph of FIG. 10 shows that in the artificial microhabitat a with enrichments of simazine-decomposing bacteria, simazine is nearly completely decomposed or degraded in about a week after the experiment started, while the graph of FIG. 9 shows that in the artificial microhabitat c without enrichments of decomposing bacteria as a comparative example, decomposition or degradation of simazine does hardly proceed even after three weeks. When the graph of FIG. 12 is compared with the graph of FIG. 11, it is shown that the same applies to the artificial microhabitat b with enrichments of decomposing bacteria and the artificial microhabitat d without enrichments of decomposing bacteria. From these findings, it is understood that by burying artificial microhabitats with enrichments of decomposing bacteria in soil for the emergence of decomposing activities of the bacteria, groundwater can be prevented from being contaminated by agricultural chemicals.

As described above, according to the present invention, it is possible to carry out enrichment and isolation of soil-inhabiting decomposing bacteria at high speeds. Hence, this invention can greatly contribute to development of a technique of utilizing contaminant-decomposing bacteria to prevent groundwater pollution caused by agricultural chemicals or the like.

What is claimed is:

1. A method of enriching bacteria in a target soil capable of decomposing organic contaminants, the method comprising the step of:

mixing a fragmented porous material, said material having a number of micropores sufficient to provide a specific surface area greater than approximately 50 $m^2/g$ and smaller than approximately 600 $m^2/g$ and having a greater adsorptivity for absorbing said organic contaminants than said target soil, into said soil which said bacteria inhabit to form an enrichment soil layer; and circulating through said enrichment soil layer an inorganic salt medium containing carbon and nitrogen sources, said carbon and nitrogen sources being formed by only said organic contaminants to be decomposed, thereby enriching said bacteria in said fragmented porous material.

2. The method according to claim 1, wherein charcoal is used as said porous material.

3. A method of isolating bacteria by making use of the enrichment method as set forth in claim 1, the method comprising the steps of:

inoculating a fragmented porous material in which said bacteria have already been enriched according to claim 1 into a new fragmented porous material to form an enrichment layer consisting of the fragmented porous materials only; and repeatedly carrying out a plurality of times an operation of enriching said bacteria in said new fragmented porous material as well by circulating through said enrichment layer an inorganic salt medium containing a carbon source and a nitrogen source, said carbon source and said nitrogen source being formed by only an organic contaminant to be decomposed, thereby increasing a degree of purity and enrichment of said bacteria, for speedy isolation of said enriched bacteria.

4. The method according to claim 2, wherein a volume ratio of volume of micropores of said porous material having pore sizes permitting said bacteria to enter into the micropores and colonize therein, to a total volume of micropores of said porous material is equal to or larger than 10%.

5. The method according to claim 4, wherein charcoal is used as said porous material.

6. A method of isolating bacteria by making use of the enrichment method as set forth in claim 4, the method comprising the steps of:

inoculating a fragmented porous material in which said bacteria have already been enriched according to claim 4 into a new fragmented porous material to form an enrichment layer consisting of the fragmented porous materials only; and repeatedly carrying out a plurality of times an operation of enriching said bacteria in said new fragmented porous material as well by circulating through said enrichment layer an inorganic salt medium containing a carbon source and a nitrogen source, said carbon source and said nitrogen source being formed by only an organic contaminant to be decomposed, thereby increasing a degree of purity and enrichment of said bacteria, for speedy isolation of said enriched bacteria.

7. A method of enriching bacteria in a target soil capable of decomposing organic contaminants, the method comprising the step of:

mixing a fragmented porous material, said material having a number of micropores and a greater adsorptivity for absorbing said organic contaminants than said target soil, into said soil which said bacteria inhabit to form an enrichment soil layer; and circulating through said enrichment soil layer an inorganic salt medium containing carbon and nitrogen sources, said carbon and nitrogen sources being formed by only said organic contaminants to be decomposed, thereby enriching said bacteria in said fragmented porous material;

wherein a volume ratio of volume of micropores of said porous material having pore sizes permitting said bacteria to enter into the micropores to a total volume of micropores of said porous material is equal to or larger than 10%.

8. The method according to claim 7, wherein charcoal is used as said porous material.

9. A method of isolating bacteria by making use of the enrichment method as set forth in claim 7, the method comprising the steps of:

inoculating a fragmented porous material in which said bacteria have already been enriched according to claim 7 into a new fragmented porous material to form an enrichment layer consisting of the fragmented porous materials only; and repeatedly carrying out a plurality of times an operation of enriching said bacteria in said new fragmented porous material as well by circulating through said enrichment layer an inorganic salt medium containing a carbon source and a nitrogen source, said carbon source and said nitrogen source being formed by only an organic contaminant to be decomposed, thereby increasing a degree of purity and enrichment of said bacteria, for speedy isolation of said enriched bacteria.

* * * * *

UNITED STATES PATENT AND TRADEMARK OFFICE
CERTIFICATE OF CORRECTION

PATENT NO.    : 6,451,580 B1                                          Page 1 of 1
DATED         : September 17, 2002
INVENTOR(S)   : Takagi et al.

It is certified that error appears in the above-identified patent and that said Letters Patent is hereby corrected as shown below:

<u>Title page,</u>
Item [73], Assignees should read:

-- [73] Assignees:    Toyo Denka Kogyo Co., Ltd., Kochi; National Institute for Agro-Environmental Sciences, Independent Administrative Institute, Tsukuba, all of (JP) --

Signed and Sealed this

First Day of July, 2003

JAMES E. ROGAN
*Director of the United States Patent and Trademark Office*